United States Patent [19]

Lorenzi et al.

[11] Patent Number: 4,641,529
[45] Date of Patent: Feb. 10, 1987

[54] PIPELINE INSPECTION DEVICE USING ULTRASONIC APPARATUS FOR CORROSION PIT DETECTION

[75] Inventors: Donald E. Lorenzi; Helmut F. Wagerer, both of Des Plaines; Lev Spevak, Chicago, all of Ill.

[73] Assignee: Magnaflux Pipeline Services, Inc., Stamford, Conn.

[21] Appl. No.: 599,481

[22] Filed: Apr. 12, 1984

[51] Int. Cl.⁴ .............................................. G01N 29/04
[52] U.S. Cl. ........................................ 73/601; 73/623; 73/644
[58] Field of Search ............... 73/601, 623, 644, 633, 73/634

[56] References Cited

U.S. PATENT DOCUMENTS

| | | |
|---|---|---|
| 3,780,571 | 12/1973 | Wiesener .............................. 73/623 |
| 3,810,384 | 5/1974 | Evans ................................... 73/623 |
| 4,285,242 | 8/1981 | Braithwaite ......................... 73/623 |
| 4,326,155 | 4/1982 | Griebeler ............................. 73/597 |
| 4,412,315 | 10/1983 | Flournay ............................. 73/623 |
| 4,418,574 | 12/1983 | Flournay ............................. 73/601 |
| 4,460,920 | 7/1984 | Weber et al. ....................... 73/623 |

Primary Examiner—Howard A. Birmiel
Attorney, Agent, or Firm—Neuman, Williams, Anderson & Olson

[57] ABSTRACT

A pipeline inspection apparatus is disclosed for the detection of corrosion pit type defects, employing one or more ultrasonic transducers to produce a parallel beam for direction toward the pipe wall from inside a pipe, with a sufficiently large beam width to permit comparison of time displayed signal components in defect depth determination, with the signal propagating through a gaseous medium. An additional embodiment combines the same with photographic apparatus.

6 Claims, 5 Drawing Figures

PIPELINE INSPECTION DEVICE USING ULTRASONIC APPARATUS FOR CORROSION PIT DETECTION

This invention relates to a pipeline inspection device and more particularly to a pipeline inspection device which incorporates ultrasonic apparatus and which is so constructed as to provide highly sensitive and reliable indications of corrosion pits. The device also includes photographic apparatus which is controlled from the ultrasonic apparatus and which operates in conjunction therewith to obtain enhanced performance.

BACKGROUND OF THE INVENTION

The detection of defects in underground or underwater pipelines is a problem which has been solved in part by the use of an inspection device using photographic apparatus such as disclosed in the O'Connor et al U.S. Pat. No. 4,373,658, issued Feb. 8, 1983. That device has a number of very important advantages over previously proposed inspection devices having photographic apparatus or other types of defect detecting apparatus, including ultrasonic systems. However, the use of photography has an important limitation when inspecting long lengths of pipeline in that there are limitations on the amount of film which can be carried and there are also limitations in the energy which is available, especially when batteries are used as the energy source.

With regard to ultrasonic inspection systems, they are well known but have not been used to any substantial extent in internal pipe inspection because of recognized limitations thereof. In a typical pulse-echo type of system, an electronic signal generator is provided which generates pulses or periodic wave trains and a sending transducer responds thereto to emit a burst of ultrasonic energy. A couplant is required to transfer energy from the sending transducer to the test piece. A receiving transducer is provided to receive and convert energy reflected back on the interior of the test piece and develop corresponding electrical signals. In many cases, the same transducer is used as both a sending transducer and a receiving transducer. When a separate receiving transducer is provided, a couplant is required between it and the test piece. A display or indicating device, typically a cathode ray tube, is associated with the detector means to produce indications of reflections from internal flaws in the test piece.

Such systems have many advantages but have the well known limitation that a liquid or solid-contact coupling is needed to provide effective transfer of ultrasonic energy between transducers and the parts being inspected. A liquid or solid-contact coupling is needed because sonic waves are highly attenuated in a gaseous medium, especially at higher frequencies, and because sonic waves are almost completely reflected at metal-gas interfaces, whereas only partial reflection occurs at metal-liquid or metal-solid interfaces and sufficient energy may be transmitted for detection of defects within the part. It is apparently because of this well known limitation of ultrasonic systems that they have not been used to any substantial extent in internal pipe testing, it being noted that it is very difficult to provide a liquid or solid-contact coupling between an ultrasonic transducer and the inside of a pipe, especially when the transducer is to be moved along the pipe and when the pipe may have weld beads or other protrusions or irregularities in its inside surface.

SUMMARY OF THE INVENTION

This invention was evolved with the general object of improving the accuracy and reliability of detection and defects in pipelines or the like.

An important aspect of the invention relates to the discovery that the use of ultrasonics for detection of defects is not necessarily limited to the use of a liquid or solid-contact coupling and that air or another gaseous medium may be used as a coupling medium. This is contrary to what was previously thought to be the case, particularly with respect to known characteristics of an interface between a gaseous medium and a solid-contact and the known effects of frequency on attenuation in a gaseous medium.

In particular, it is known that the amount of energy reflected at an interface between two media is a function of differences in the acoustic impedances in the two media and since there is a large difference between the acoustic impedances in a gaseous medium and that in most solids, especially metals, a very high portion of energy is reflected at an interface. This would seem to prohibit the use of intervening gaseous media between a transducer and a metal part.

It is also known that while the attenuation of ultrasonic energy in air may be affected by humidity and other factors, a primary component of attenuation in air or any other gaseous medium increases as the square of frequency. This would indicate that if an attempt were made to transmit through a gaseous medium, the frequency would have to be so low as to prevent detection of small defects since it would result in a wavelength much larger than the defect depth, wavelength being inversely proportional to frequency.

It is found, however, that the detection of corrosion pits does not require penetration of energy into the part. It is found that corrosion pits may contain reflecting liquids and/or particulate solids such as those resulting from the corrosion process but to the extent that reflections are produced, they do not have the same timing as reflections from surrounding areas. In most cases, the ultrasonic energy is propagated to the bottom surface of the pit which produces a relatively strong reflection in delayed relation to the reflection from the surrounding surface.

It is also found that the use of a high frequency is not only possible but enhances the operation in a number of respects. In particular, the use of a high frequency results in a short wavelength of propagation and, when a properly damped transducer is used, the electrical signals from a corrosion pit and from a surrounding surface area are of short duration and distinguishable, even though the depth of the pit may be quite small. Also, by restricting the beam area, the signal components from reflections from the bottom surfaces of pits may have an amplitude comparable to the amplitude of signal components from reflections from surrounding surface areas.

In accordance with this invention, transducer means are provided for responding to an energizing signal to propagate ultrasonic energy through a gaseous medium toward a surface portion of a test object and for developing a received signal from ultrasonic energy reflected back from the surface portion, with detector means being provided for responding to the received signal and for indicating the presence of any recessed defect of a type having a bottom surface which is recessed in relation to the surrounding surface portion of the object.

In accordance with a specific feature, the wavelength of the propagated ultrasonic energy is substantially less than the depth of recessed defects to be detected. Preferably, the ultrasonic energy is transmitted and received at a frequency of on the order of 500 KHz. In any case, the frequency is high enough to permit signal components from bottom surfaces and signal components from surrounding surface areas to be distinguished, while being low enough to obtain signal components of adequate amplitude to be amplified and distinguished.

The size of the transducer, the spacing between the transducer and the part and the character of any focusing device used is such as to obtain an effective beam width at the surface of the part which is of the same order of magnitude as the width dimension of the corrosion pits to be detected.

Further important features relate to the provision of circuitry such that the signal components from pits can be readily distinguished from other signal components.

The transducer is preferably carried by a "pig" device of the type used for cleaning of pipelines, and the transducer is preferably located at a protected position in proximity to one of the cups of the pig. The pig is preferably so weighted as to place the transducer at a "6 o'clock" position for detection of corrosion pits which are typically located in the lowermost portions of a pipe.

In one embodiment of the invention, a transducer is supported for movement in a transverse direction, preferably being supported for pivotal movement about the pipe axis, with a motor being provided for effecting such movement. The motor may spin the transducer about the pipe axis, or may be used to effect pivotal oscillatory movement of the transducer or may place the transducer at a fixed angular position when no movement is desired.

In another embodiment, a plurality of transducers are used which may be fixedly carried on an inspection pig, for increasing the inspected area without requiring transducer movement.

Additional very important features of the invention relate to the combination of the ultrasonic apparatus with photographic apparatus. The signals produced by the ultrasonic apparatus are used to trigger operation of a camera and associated strobe lamp means, to obtain a photograph of any area in which significant corrosion pits are detected.

Further features relate to the use of recording apparatus for recording signals produced by the ultrasonic apparatus and for recording distance signals to indicate the position of detected corrosion pits and also to correlate the ultrasonic indications with the photographs produced by the photographic apparatus.

This invention contemplates other objects, features and advantages which will become more fully apparent from the following detailed description taken in conjunction with the accompanying drawings.

DESCRIPTION OF PREFERRED EMBODIMENTS

Figure 2:
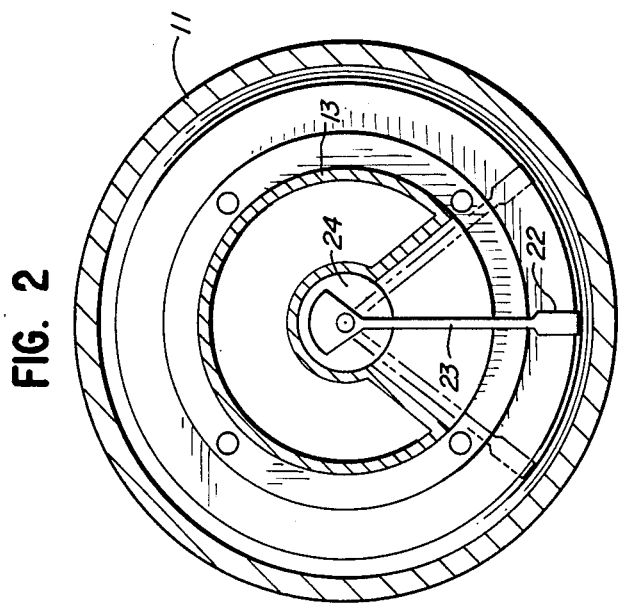
FIG. 2 is a sectional view taken substantially along line II—II of FIG. 1, particularly showing a transducer of the ultrasonic apparatus and its support.

Reference numeral 10 generally designates a pipeline inspection device constructed in accordance with the principles of this invention. The illustrated device 10 is in the form of a "pig" designed to be disposed within a pipeline 11, such as a natural gas pipeline, and to be moved along the pipeline. The device 10 includes ultrasonic inspection apparatus generally designated by reference numeral 12, and mounted in a housing section 13. It also includes photographic inspection apparatus generally designated by reference numeral 14, mounted in a housing section 15. Housing sections 13 and 15 are mounted in end-to-end relation between a forward set of cups 17 and 18 and a rearward set of cups 19 and 20. Cups 17–20 are of a resilient elastomeric material and slide along the pipeline inside surface, indicated by reference numeral 21.

The device 10 is designed to be propelled along the pipeline by pressure within the pipeline which may act directly thereon or which may act on a towing pig having a rearward end coupled to the forward end of the illustrated device. When a towing pig is used, the cups may be provided with peripheral slots or openings may otherwise be provided for application of pressure to the forward towing pig. It will be understood that other propulsion means may be used.

Figure 1:
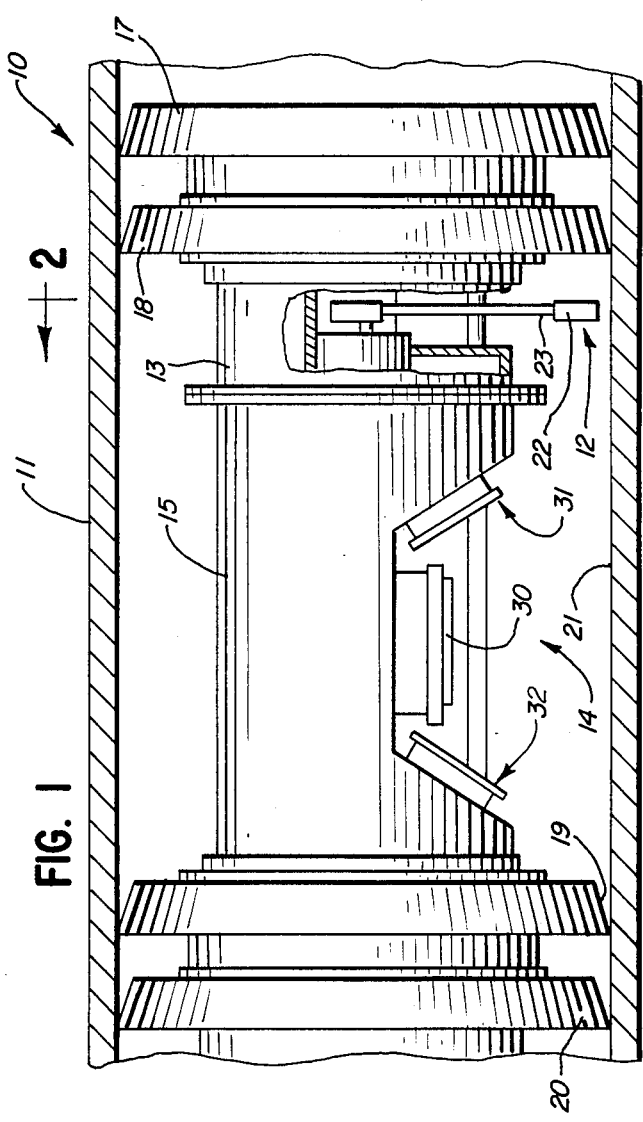
FIG. 1 is a side elevational view partly in section, illustrating a pipe inspection device constructed in accordance with the invention and including ultrasonic apparatus of the invention.

The ultrasonic inspection apparatus 12 includes a transducer 22 positioned adjacent the lower upwardly facing portion of the surface 21 and behind the rearward cup 18 of the forward set of cups. In the embodiment as illustrated in FIGS. 1 and 2, the transducer 22 is carried at the lower terminal end of an arm 23 which is carried by the shaft of a servo motor 24, for pivotal movement about an axis coincident with the longitudinal axis of the device 10 and of the pipeline 11. Servo motor 24 is operable to permit adjustment of the angular position of the transducer or to permit oscillatory scanning movement of the transducer 22.

Figure 3:
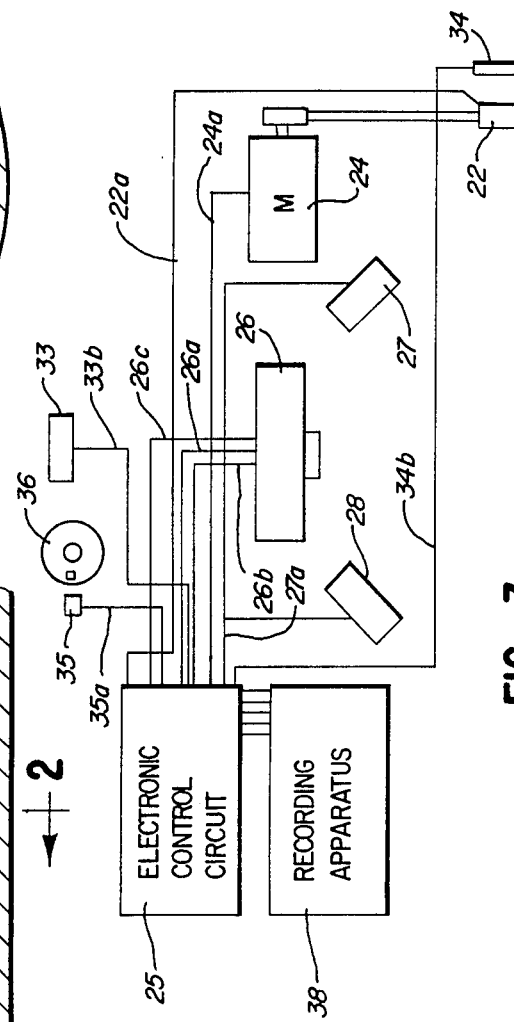
FIG. 3 is a diagrammatic illustration of the connection of the ultrasonic apparatus and associated photographic apparatus with an electronic control circuit and recording apparatus.

As shown diagrammatically in FIG. 3, the transducer 22 and the motor 24 are connected to electronic control circuitry 25 which is also connected to a camera 26 of the photographic apparatus 14, to control shutter and film-advance operations of the camera 26. The circuitry 25 is also connected to a pair of strobe lamps 27 and 28. Camera 26 is mounted behind an optical port 30 in the housing section with a viewing axis which is normal to the axis of the pipeline 11. Strobe lamps 27 and 28 are mounted behind ports 31 and 32, located in slanted portions of the housing section 15. Only one strobe lamp need be used, if desired.

As is also shown diagrammatically in FIG. 3, the electronic control circuitry 25 may also be connected to a weld sensing device 33 and also to a magnetic defect detecting device 34 which is mounted forwardly from the camera to detect flaws. Also, a pick-up device 35 is connected to the circuitry 25 and is mounted adjacent a wheel 36 which carries one or more peripheral magnets to generate pulses in the pick-up device 35 during rotation of the wheel 36. The wheel 36 is engaged with the inside pipe surface 21 so that each pulse represents a predetermined incremental distance of travel. The pick-up device 35 and wheel 36 may preferably be part of an optical port wiper assembly which is not shown but which may have a construction as disclosed in U.S. Pat. No. 4,363,545, issued Dec. 14, 1982.

The device 10 is desirably capable of traveling for many miles in a pipeline and to conserve electrical energy and also to conserve film, it is desirable that photographs be taken only of regions where defects are present which are of a serious nature such as to require possible corrective action. For this reason, the device 10 includes weights associated with the forward and rearward cup assemblies to place the viewing axis at a "6 o'clock" position so as to obtain photographs of only the lower, upwardly facing portion of the internal surface 21. The weights are not shown but are located as disclosed in U.S. Pat. No. 4,372,658, issued Feb. 8, 1983.

Also, the photographic apparatus is controllable from the weld sensing device 33, the magnetic detector device 34 and the ultrasonic inspection apparatus 12 in a manner such as to restrict the operation of the photographic apparatus to areas in the vicinity of welds, to areas in which defects are magnetically detected and areas in which corrosion pits are detected by the ultrasonic apparatus 12. It is noted that the ultrasonic transducer 22 is positioned adjacent the lower portion of the surface 21 in a region in which corrosion pits are most apt to occur. Corrosion typically takes place where there is free water in the lower portion of the pipeline, capable of combining with carbon dioxide to produce carbonic acid. It is also noted that the transducer 27 is located adjacent the cup 18 in a protected position within the protective chamber which is provided between the rearward and forward cups and which facilitates obtaining of clear photographs of the pipe surface.

The combination of the ultrasonic apparatus with the photographic apparatus is highly advantageous not only in preventing unnecessary waste of film and energy but also in providing two sources of information with respect to the existence or non-existence of corrosion pits. The ultrasonic apparatus 12 is connected to recording apparatus 38 operable to record indications of corrosion pits, produced by the ultrasonic apparatus. The recording apparatus 38 is also connected to the weld sensing device 33, and magnetic detector device 34 and also to the pick-up device 35 and signals from the pick-up device 35 are also applied to the camera for recording of distance information in connection with the film. By correlating and comparing the various indications obtained, it is possible to obtain highly accurate and reliable information with respect to the existence or non-existence of corrosion pits and to establish whether there is any problem which requires remedial action. The photographic apparatus 14 develops a record usable for monitoring the operation of the ultrasonic apparatus 12 and for interpreting and verifying the indications produced by the ultrasonic apparatus. Similarly, the ultrasonic apparatus 12 is usable for monitoring and interpreting the photographic records produced by the apparatus 14. The combination of the ultrasonic apparatus 12 with the photographic apparatus 14 is thus highly advantageous and is a very important aspect of the invention, but it will be understood that the ultrasonic apparatus 12 may be used alone for the detection of corrosion pits, and need not be combined with the photographic apparatus 14, or any other type of inspection apparatus.

Figures 4, 5:
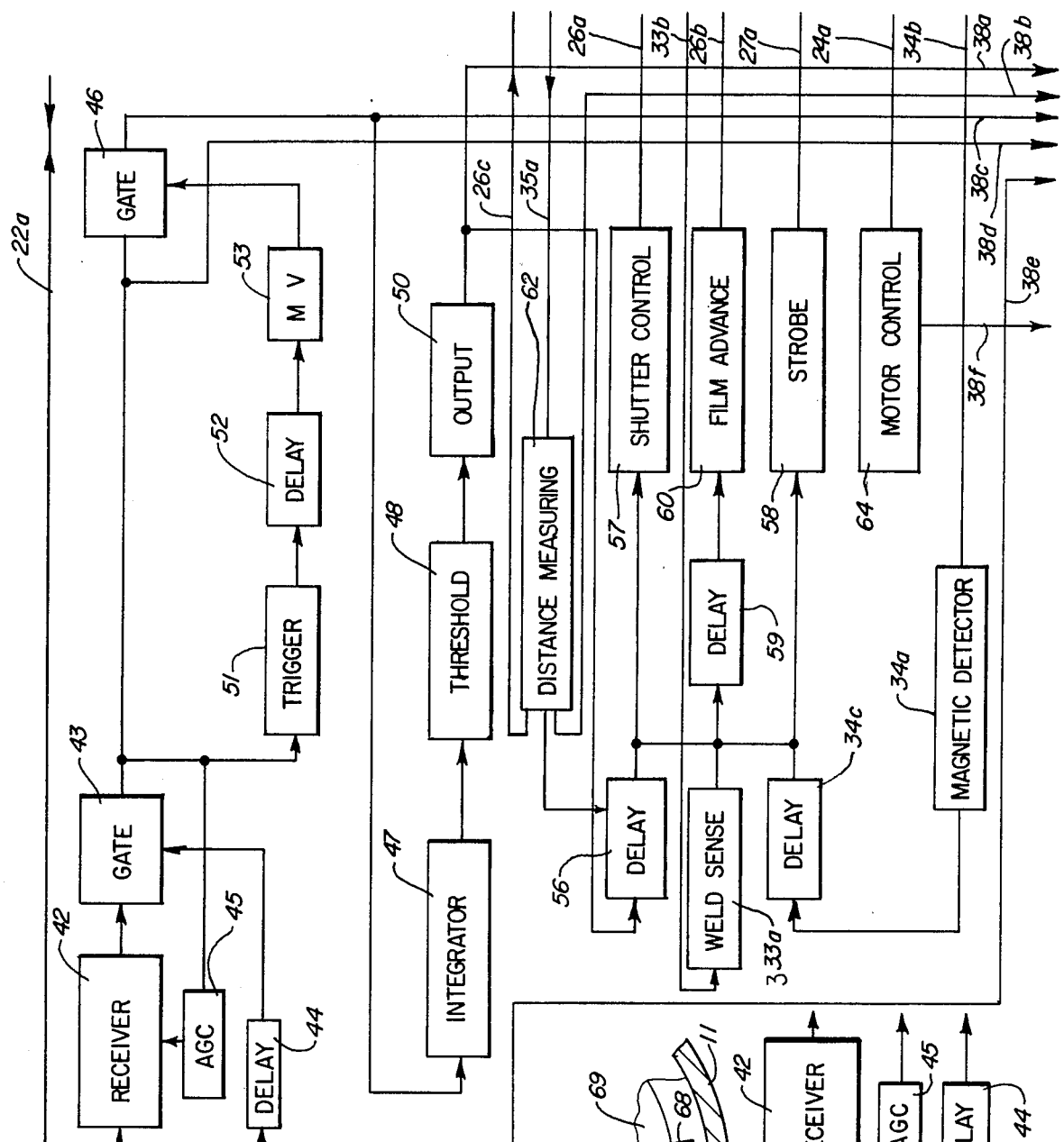
FIG. 4 is a schematic diagram of the electronic control circuit which is illustrated in block form in FIG. 3.
FIG. 5 is a partial sectional view similar to part of FIG. 2 diagrammatically illustrating a modified arrangement using a plurality of fixed transducers and also showing the electrical circuitry connected thereto.

FIG. 4 is a schematic block diagram of the electronic control circuit 25. A pulser 40 is controlled by a clock 41 to periodically apply pulses through a line 22a to the transducer 22 at a repetition rate of on the order of 2 KHz, for example. Signals developed by the transducer from reflections from the surface of the pipe and corrosion pits therein are amplified by a receiver 42 and are applied to a gate circuit 43 which is controlled through a delay circuit 44 from the clock 41. The gate circuit 43 is operative to transmit signals only during time intervals when reflected signals from the internal surface of the pipe would normally be expected. Thus, the delay time interval should be on the order of twice the minimum spacing distance between the transducer and the pipe surface divided by the velocity of propagation in the gaseous medium within the pipeline. The delay circuit 44 may include means for disabling the gate circuit a short time interval after it is enabled, sufficient for the maximum spacing distance and detection of the bottom surfaces of corrosion pits of maximum depth.

The output of the gate circuit 43 is applied to an automatic gain control circuit 45 for the receiver 42. In addition, it is coupled through a gate circuit 46 and through an integrator circuit 47 through a threshold circuit 48 which has its output connected to an output circuit 50. Gate circuit 46 is controlled to operate during a time interval of short duration, in timed relation after the leading edge of a signal component developed by reflection from the surface of the pipe. For this purpose, the output of the gate circuit 43 is applied to a trigger circuit 51 which initiates operation of a delay circuit 52, the output of the delay circuit 52 being applied to a monostable multivibrator 53 which controls the gate circuit 46. The delay provided by the delay circuit 52 and the duration of operation of the monostable multivibrator 53 are such as to produce maximum response to signal components derived from the bottom surfaces of corrosion pits, such signal components being delayed slightly in relation to signal components derived from reflections from the surface portions which surround the pits. It is noted that although the effective beam width of the transducer at the surface of the pipe is preferably quite narrow, it is wide enough that components from corrosion pits and components from the surrounding surface areas are produced in response to each transmitted burst of ultrasonic energy.

The gated signal components produced at the output of the gate circuit 46 are integrated by the integrator circuit 47 which may have an effective time constant equal to several transmit-receive cycles but short enough in relation to the scanning velocity to permit detection of single corrosion pits.

When the output of the integrator circuit 47 exceeds a certain threshold value, the threshold circuit 48 develops a signal which is applied to the output circuit 50. The output circuit 50 is connected to a delay circuit 56 which applies a delayed signal to a camera shutter control circuit 57, to a strobe control circuit 58 and to a delay circuit 59 which is connected to a film advance circuit 60. Circuits 57 and 60 are connected to the camera 26 through lines 26a and 26b which circuit 58 is connected to the strobe lamps through line 27a. The inputs of circuits 57, 58 and 59 are also connected to the outputs of a weld sense circuit 33a and a magnetic detector circuit 34a, the input thereof being connected through lines 33b and 34b to the sensing and detector devices 33 and 34. A delay circuit 34c may be provided at the output of circuit 34a.

The delay produced by the delay circuit 56 is such as to produce a photograph of any area of the surface of the pipe which has a detected corrosion pit therein. To adjust for variations in the speed of travel, delay circuit 56 is connected to a distance measuring circuit 62 which is connected through a line 35a to the pick-up device 35, the delay being controlled to be inversely proportional to the speed of travel.

The recording apparatus 38 which may be a multi-track magnetic tape recorder, for example, has an inputs 38a connected to the output of the output circuit 50 and also has an input connected through a line 38b to an output of the distance measuring circuit 62, the recorded signals being such that the position of the detected corrosion pits may be determined. The distance measuring circuit 62 may also have an output connected through a line 26e to means within the field of view of the camera or means within the camera, operative to record distance information on each frame of the film.

In addition to recording the output signals produced by the output circuit 50, the recording apparatus 38 may have inputs connected through lines 38c and 38d to the outputs of the gate circuits 46 and 43 and through a line 38e to an output of the clock circuit 41 for recording of signals which may be reproduced and applied to an oscilloscope, for example, for analysis.

The recording apparatus 38 is additionally connected through a line 38f to a motor control circuit 64 which is connected through a line or cable 24a to control operation of the motor 24. The motor control circuit 64 may, for example, effect oscillatory scanning movements of the transducer 22 in a direction transverse to the pipe axis. Circuitry similar to that disclosed in the Flaherty et al U.S. Pat. No. 3,403,671, issued Oct. 1, 1968, may be used for this purpose. Alternatively, the motor control circuit 64 may be used to simply adjust the angular position of the transducer.

The arrangement as illustrated in FIGS. 1 and 2 may be operated with the motor 24 de-energized and with the transducer 22 maintained in a fixed angular position relative to the support structure and thereby at a substantially fixed angular position relative to the pipeline, the device being weighted as aforementioned. A "6 o'clock" position is preferred since corrosion pits are generally produced at the lowermost portion of the pipe.

It is also possible to use a plurality of fixed transducers. FIG. 5 illustrates a modification in which three transducers 66, 67 and 68 are secured on a support member 69 which may be fixedly mounted between the rearward side of the rearward forward cup, the rearward side of the forward cups 17 and 18 and the forward end of the housing section 15, in place of the housing section 13. As shown, transducer 67 is at a "6 o'clock" position while transducers 66 and 68 have opposite angular offsets from the "6 o'clock" position.

Transducers 66, 67 and 68 are connected to a switching circuit 70 to be sequentially connected to the pulser 40 and the receiver 42. The switching circuit 70 is connected to the clock 41 and includes circuitry such that the switching is performed in synchronism with the pulsing of the transducers, either at the same rate or at a submultiple rate. As one example, the pulse repetition rate may be 2 KHz and in each switching cycle a single pulse may be transmitted by transducer 66, then a single pulse by transducer 67 and then a single pulse by transducer 68. As another example, the pulses may be transmitted by transducer 66, then ten pulses by transducer 67 and then ten pulses by transducer 68.

The circuitry in FIG. 5 is otherwise like that shown in FIG. 4, except that a signal from the switching circuit 70 is applied to the recording apparatus 38, through a line 38g.

The provision of a plurality of transversely spaced transducers, as shown in FIG. 5, has the advantage of increasing the effective width of operation of the transducer assembly and thereby the effective width of the area which is inspected, without requiring a moving transducer. It will be understood that the transverse width of each of one or more transducers may be increased or adjusted, as required, and also that additional transducers may be used.

It may also be desirable to increase the effective longitudinal dimension of the region of operation of the transducer assembly, either by increasing the longitudinal dimension of each transducer or by providing longitudinally spaced transducers. Increasing the effective longitudinal dimension may be desirable to detect a reflected burst of ultrasonic energy at a position shifted longitudinally from the position from which it was transmitted. When the device is moving through a pipe and/or when the gaseous medium is flowing in the pipe, the gaseous medium between the transducer assembly and the pipe surface may have a net longitudinal velocity relative to the device and there may be a corresponding longitudinal displacement of the position of return of a reflected burst of energy relative to the position of transmission of the burst. Accordingly, either the longitudinal dimension of a transmitting-receiving transducer may be increased or a pair of longitudinally spaced transmitting and receiving transducers may be used, operating with a "pitch-catch" method. When separate transducers are used, the spacing and/or angles thereof may be adjusted or dynamically controlled according to operating conditions.

When a plurality of transmitting-receiving transducers or transducer pairs are used, a plurality of transducer energizing and received signal detector circuits may be provided, each having a construction like that shown in FIG. 4 and each being connected to only one transmitting-receiving transducer or transducer pairs or through a switching circuit, to a plurality of transducers, as shown in FIG. 5. The output signals from a plurality of such energizing and detector circuits may be combined to operate the photographic apparatus when any corrosion pit is detected or when the integrated value or summation of a plurality of output signals within a certain time interval exceeds a certain threshold value.

By way of example, the transducer 22 (or each of the transducers 66–68 in the FIG. 5 embodiment) may comprise a single PZT plate having a thickness such as to obtain a natural resonant frequency of on the order of 0.5 MHz and having width dimensions of on the order of 1 CM., the transducer being provided with suitable damping. The nominal spacing between the transducer and the surface of the pipe may be of on the order of 5 CM. and the effective beam width at the surface of the pipe may be only slightly larger than the width of the transducer plate. In any case, the effective beam width is desirably longer than the width of corrosion pits so that signal components are obtained from both the bottom surface of a pit and the surrounding surface areas, for comparison purposes. At the same time, the beam width should be small enough that the amplitudes of such signal components are of the same order of magnitude.

It will be understood that modifications and variations may be effected without departing from the spirit and scope of the novel concepts of this invention.

We claim:

1. In a device for pipeline inspection, ultrasonic apparatus including ultrasonic transducer means for transmitting ultrasonic energy to the internal surface of a pipeline and for receiving energy therefrom to develop electrical signals, and detector means for responding to said electrical signals to produce output signals in response to corrosion pits in said internal surface of the pipeline, photographic apparatus for producing a photograph of a portion of the internal surface of the pipeline, support and drive means for supporting said ultrasonic apparatus and said photographic apparatus for movement within the pipeline, and control means for controlling operation of said apparatus from output signals of said detector means to produce photographs of portions of the pipeline having corrosion pits detected by said ultrasonic apparatus, said support and drive means comprising a central housing section, and forward and rearward resilient cup means secured to forward and rearward ends of said central housing section, said photographic apparatus being supported in said central housing section to operate in a protected space between said forward and rearward cup means, said ultrasonic transducer means being located between said forward and rearward cup means, and said ultrasonic transducer means being located behind said forward cup means and forwardly with respect to said photographic apparatus, and delay means for responding to said output signals to operate said photographic apparatus after a time delay approximately equal to the time required for said device to travel a distance equal to the longitudinal distance from said ultrasonic transducer means to a central viewing axis of said photographic apparatus.

2. In a device as defined in claim 1, for operation in a pipeline containing air or another gaseous medium, said transducer means being supported by said support and drive means in spaced relation to the inside surface of the pipeline during movement therein and being operative to transmit and receive ultrasonic energy through the gaseous medium within the pipeline.

3. In a device as defined in claim 2, said ultrasonic transducer means being operable to transmit and receive ultrasonic energy having a frequency of on the order of 500 KHz.

4. In a device as defined in claim 1, recording means for recording signals developed by said ultrasonic apparatus, the recorded signals being comparable with photographs produced by said photographic apparatus for verification of indications of corrosion pits and for otherwise facilitating analysis of photographs produced by said photographic apparatus.

5. Ultrasonic apparatus for detection of corrosion pits or like relatively shallow defects having bottom surfaces which are recessed in relation to surrounding surface portions of an object under test, generator means for generating an energizing signal, transducer means for responding to said energizing signal to propagate ultrasonic energy in a beam through air or another gaseous medium and directly toward a surface portion of the test object and for developing a received signal from ultrasonic energy reflected back in said beam from said surface portion, detector means for responding to said received signal and for indicating the presence of a recessed defect in said surface portion, and support means supporting said transducer means for movement along said surface of the test object with a nominal spacing from said surface which is sufficiently large for non-contacting movement over irregularities therein, said beam of ultrasonic energy being a parallel beam propagated along an axis normal to the surface of the object, the effective width of said parallel beam being large enough to obtain two time-displaced received signal components for comparison to determine the depth of a defect, one received signal component being obtained from the bottom surface of a defect and the other being obtained from a surrounding surface area of the object, and the wavelength of the ultrasonic energy being substantially less than the depth of recessed defects to be detected while being large enough to permit propagation of said parallel beam through air or another gaseous medium and obtain a received signal in which both of said received signal components are of sufficient amplitude for comparison purposes.

6. In ultrasonic apparatus as defined in claim 5, the wavelength of said ultrasonic energy and the width of said beam being on the order of those obtained with a transducer in the form of a single piezoelectric plate having a natural resonant frequency of 0.5 MHz and having a width of 1 CM.

* * * * *